(12) United States Patent
Postrel

(10) Patent No.: US 12,303,259 B2
(45) Date of Patent: May 20, 2025

(54) COMPREHENSIVE HEALTH STATUS BY SIMULTANEOUSLY READING VOLATILE AND NON-VOLATILE COMPOUNDS

(71) Applicant: Richard Postrel, Miami Beach, FL (US)

(72) Inventor: Richard Postrel, Miami Beach, FL (US)

(73) Assignee: VOC Health, Inc., Miami Beach, FL (US)

( * ) Notice: Subject to any disclaimer, the term of this patent is extended or adjusted under 35 U.S.C. 154(b) by 805 days.

(21) Appl. No.: 17/609,347

(22) PCT Filed: Sep. 30, 2021

(86) PCT No.: PCT/US2021/052994
§ 371 (c)(1),
(2) Date: Nov. 5, 2021

(87) PCT Pub. No.: WO2022/072714
PCT Pub. Date: Apr. 7, 2022

(65) Prior Publication Data
US 2023/0248269 A1     Aug. 10, 2023

Related U.S. Application Data

(60) Provisional application No. 63/085,077, filed on Sep. 29, 2020.

(51) Int. Cl.
*A61B 5/145* (2006.01)
*A61B 5/1455* (2006.01)

(52) U.S. Cl.
CPC ...... *A61B 5/14507* (2013.01); *A61B 5/14546* (2013.01); *A61B 5/1455* (2013.01); *A61B 2562/12* (2013.01)

(58) Field of Classification Search
CPC ... A61B 5/145; A61B 5/1455; A61B 5/14551; A61B 5/14552; A61B 5/14532; A61B 5/14546; A61B 5/14507; A61B 5/1451; A61B 5/14539; A61B 5/14542; A61B 5/1468; A61B 5/1486
See application file for complete search history.

(56) References Cited

U.S. PATENT DOCUMENTS

| | | | | |
|---|---|---|---|---|
| 8,192,360 B2 * | 6/2012 | Koh | ...... | A61B 5/0084 600/324 |
| 10,925,523 B2 * | 2/2021 | Rogers | ...... | A61B 5/14542 |

* cited by examiner

*Primary Examiner* — Chu Chuan Liu

(57) ABSTRACT

The present invention provides an improved system, device, and method for determining a comprehensive state of health in real time using non-invasive patient testing. The invention characterizes disease and other states of health by simultaneously assaying both liquid and gas in a sample or samples. During metabolism, the body performs a large variety of biochemical reactions. Reaction products, reaction by-products, and breakdown products are transported by the circulatory system throughout the body. Many of these molecular products are labile and volatilize into gases from bodily liquids. In gas form, these compounds appear as volatile organic compounds (VOCs).

38 Claims, No Drawings

COMPREHENSIVE HEALTH STATUS BY SIMULTANEOUSLY READING VOLATILE AND NON-VOLATILE COMPOUNDS

The present invention provides an improved system, device, and method for determining a comprehensive state of health in real time using non-invasive patient testing. The invention characterizes disease and other states of health by simultaneously assaying both liquid and gas in a sample or samples. During metabolism, the body performs a large variety of biochemical reactions. Reaction products, reaction by-products, and breakdown products are transported by the circulatory system throughout the body. Many of these molecular products are labile and volatilize into gases from bodily liquids. In gas form, these compounds appear as volatile organic compounds (VOCs). Less labile molecules, generally those with a molecular weight (MW)>~300 g/mol, remain dissolved in the body's liquids, e.g., saliva, tears, plasma, urine, etc. Analysis of the patient's VOCs provides multitude of multidimensional information relating to the body's metabolism, including, but not limited to metabolism of pathogenic and non-pathogenic organisms hosted in the body, the body's responses to the foreign organisms, metabolism of the body' organs and tissues, loss of function, (auto)immunological events, aging, nutrition, etc. Liquid biosamples are available with only slight contact with the body, e.g., by collecting urine, plasma, saliva, mucus, sweat, tears, etc. The typically larger molecules that do not readily volatilize provide a collaborative, potentially synergistic wealth of metabolic information of a person's comprehensive health status. Use of the present invention may reduce the number and extent of invasive medical procedures through the early identification and detection of disease.

A comprehensive analysis as obtainable in accordance with this invention provides a multi-faceted picture of a person's health status at that specific point in time, for example, damage from an injury, toxic exposure, presence of infection, etc., and monitoring the body's progress or lack thereof in managing such challenges and changes. Periodic sampling from a single individual easily provides a longitudinal documentary of that individual's health over time. Comparison with a baseline obtained before treatment allows periodic assessment of treatment efficacy and/or its progress. A baseline and subsequent tests during during routine physicals can signal changes in a person's health and suggest possible compensatory, proactive, or prophylactic steps to be considered. Periodic routine tests may detect an asymptomatic disease such as a cancer at its earliest stage, where treatment is historically most effective. For slowly progressing cancers, and for those persons at high risk of aggressive treatment, scheduled follow-on testing can help the patient decide his or her best course of management. Following treatment for a potentially recurring disease such as HIV, rickettsia , cancer, etc., a physician or other health care professional may prescribe or suggest a testing protocol as provided by this invention. For insurance carriers, health care managers, and financial planners, longitudinal assessments provided by repeated testing can help plan for viatical and lifestyle changes.

The device is capable of processing liquid samples and its off-gasses from a single source. Thus, rather than monitoring VOCs or liquid samples, the present invention includes embodiments that assay larger or non-volatile compounds captured in a liquid carrier or solvent, while simultaneously analyzing lighter volatile components evaporated from the same or duplicate liquid. A device may combine both liquid and gas analysis sensor arrays in one unit or separate units which reconcile and unify the collected data during analysis.

The liquid analysis module assays individual chemical components including, but not limited to: peptides/proteins, fatty acids and other lipids, metalloproteins, lipoproteins, phospholipids, hormones, other messenger compounds, nucleic acid fragments, etc. The gaseous analysis module accepts gases (e.g., VOCs) from the liquid analysis module (or a separate fraction thereof) thereby combining and relating data from these disparate analytical methods within a single cross-correlative machine-learning/artificial-intelligence enabled reporting.

In accord with this novel approach, the present invention features a process and method for a rapid, on-site high throughput screening for unhealthy conditions or the specific identification of one or more disease(s) using a single, non-invasively obtained bio-sample. The invention further provides a process that optimizes data capture, classification, and pattern recognition that is necessary for classifying and identifying distinct volatile organic compound (VOC) signatures from bio-samples while simultaneously capturing corresponding data relating to the less volatile molecules present in the liquid that provides off-gassed VOCs. This invention thereby enables recognition/characterization/identification of a disease from the earliest onset point of that disease and may shed light on how the disease was initiated, e.g, pathogenic attack, nutritional requirements, toxic exposure, incompatible microbiome, mutated enzyme, etc. In selected embodiments this invention may screen for environmental exposure(s) and/or general health with the object of earlier treatment to improve patient outcomes and experiences.

Clinical Onset

Multiple embodiments of this invention require integrated circuitry to continuously adapt the sensor parameters multiple times during a single sample assessment. The devices use data obtained from a first interaction of a molecule or a series of molecules with an individual sensor element or layer to modulate sensing parameters of neighboring sensor elements and thereby precisely characterize individual molecular components in the sample to produce a profile or instantaneous snapshot. The circuitry may adjust attraction parameters (e.g., temperature (T), base voltage, flow rate, dilution, etc.) to control bulk attraction/volatility between sensor and sample molecules and thus meter release rates of various classes of molecules into various sensor layers. On one or more levels, the device may time average and characterize information obtained from multiple compounds proximal to a sensor element using information such as a voltage (V) change, time of interaction, strength of interaction, etc., with one or a plurality of sensors to adjust sensation parameters of later interacting sensor layers or to optimize parameters for subsequent analyses.

Downstream or later interacting sensors may be instructed to provide feedback for use in longitudinal analysis and/or optimization of algorithms for future analyses. The present invention is enabled to analyze outputs from multiple sensor elements and establishing specific values for each of the bio-elements obtained from a single patient or sample. The signature or signatures obtained provide a multidimensional view of an individual patient or group pf patients to significantly improve early detection and therapeutic performance for that patient, disease, or patient group. By analyzing sequential samplings from an individual or group of individuals, the present invention allows for performance analysis that quantifies the progression or regression of a disease or treatment for that disease as prescribed. Sequential samplings and analysis may also be useful for modulating treatment protocols, with regard to duration, frequency and use of treatments to minimize undesired side effects from ongoing treatments, such as, in the case of radiation or chemotherapy, thereby allowing practitioners to more finely tune their use of individual therapies or therapies in combination. The present invention allows for the rapid assessment of a first treatment strategy to assess the efficacy of a particular treatment or the continuation or modification of that treatment to improve the quality of life and patient outcomes through earlier and more accurate detection.

Scientific Background

In general, larger molecules are less volatile than smaller molecules. In chemical terms, larger molecules tend to have a lower partial pressure at a given T and are more prone to remain in a liquid state or phase than smaller molecules. However, the skilled artisan is also aware that "likes dissolve likes" so non-polar molecules will tend to be less volatile when leaving a non-polar solvent than when leaving a polar solvent. The polarity of a chemical bond is associated with the difference in electro-negativity (affinity of the atomic nucleus for its electrons) of the two elements. An atomic dimer, e.g., $O_2$, will be non-polar since the electrons are equally shared. Water, with two O—H bonds, forms a dipole with the O portion being more negative. Alcohols and nitrogen or sulfur side groups will contribute to polarity. Thus, while in general, heavier molecules are larger and larger molecules have more surface for non-covalent bonding, e.g., van der Waals, and thus are more associative with other molecules, electron distributions specific to the bonds forming the molecules create repulsive and attractive forces determining probabilities of molecules distributing to another phase (or solvent, if using multiple solvents.

Larger molecules also have more configurations available depending on the twists and bends of their chemical bonds. Thus, in water, a larger molecule is more likely to "present" polar molecules to the polar solvent and thus internalize non-polar or less polar constituents. In the gas phase, small molecules will turn more electro-negative atoms in the molecule away from a negatively charged sensor—leaving positive ends of dipole structures to associate or be more proximal to the sensor surface. The opposite effect would obtain for positively charged sensors.

Temperature will also affect molecular shape by decreasing the association of electro-negative portions and electro-positive portions within a molecule or with molecules that dimerize, trimerize or multiply associate with like molecules. As T increases, the molecules may appear to be smaller in size as oligomeric bonds are less dominant. In such instances, heavier or less motile molecules may remain in or on a more retentive pool or sensing layer, but appear unexpectedly smaller when interacting with sensors at subsequent layers.

The system is designed to read a person's sample to produce a profile corresponding to that person. The profile is compared to profiled signatures in a library with matches indicative of the person's health status and when compiled with other data provides insight into the health concerns presented across the community of interest. When the analytical software encounters profiles that cannot be matched to any of those in the libraries, such novel sample profiles are incorporated into a development library with all available corresponding information, including but not limited to: source of sample, confirmed disease, suspected disease, symptoms, similarity of unmatchable VOCs to associative properties of known or unknown compounds (associated with a disease?), polarity, size, atomic content, parallel analyses (other VOCs whose appearances cross-correlate), serial analyses from other assays (e.g., mass-spec data, molecular weight, solubility, partitioning between solvents or solvent and gas, etc.) Such data are preferably pooled with data from multiple users of these devices for cross correlations and improving machine learning outcomes. These novel profiles, especially when confirmed by similar novel outputs, in an integrated system of e.g., hospitals, emergency clinics, routine screenings, etc., provide a system for recognizing a new disease, disease variant (mutation), bio-threat, etc., at its early appearance. Once identified as a new pathogen of interest, the genetic code of the new organism can be determined using samples from the person or persons who presented with the pathogen.

Data can be processed in real-time, making interim results available somewhat continuously during the sensing session. The interim data are useful for modulating sensor parameters if desired, for example, tracking progression of each of individual molecules through the sensing module. Data may be collated, stored and processed and/or reprocessed subsequent to initial analysis. Data from multiple analytical reads may be combined and/or compared to build on the capacities and accuracies associated with the machine learning/artificial intelligence algorithms. Especially when the device is applied to monitor progress of a disease or treatment, post sense analysis can be crucial for comparisons. Raw data from an early assessment may be reconfigured to highlight comparative data deemed significant following later assessments. Devices of the present invention can participate in a system or systems where data are compiled from multiple device sources to improve, inform and update the system's control functions, update algorithms, and/or to update signatures. Such updates may optionally be delivered to any individual device or up to all devices contributing to the system(s).

It is well understood that larger molecules are more likely to be docile on a surface or dissolved in a liquid, while smaller molecules are more likely to escape the surface of the solid or liquid and become volatile, e.g., VOCs. Longer chain molecules will tend to remain docile since they present a larger surface area for intermolecular interactions. Multi-branched 3-D, high MW, or more folded molecules will present less surface area for interaction or require greater energy to say aloft. Even though a particular molecule may be slightly heavier in MW, in certain cases, it may be more volatile than a lower MW molecule, due to shape/charge pattern. Charge (V), carrier gas, T and other features are therefore parameters the analytical algorithms may include as distinguishing variables.

The integrated circuitry responds to an initial detection by a sensor element indicative of attractive interaction with a proximate molecule to identify a class of compounds potentially interacting with that initial sensor. The circuitry then modifies attraction features (e.g., base V, T, charge change frequency, etc.) of neighboring sensor elements to assess attraction by one or more neighboring sensor elements for that same molecule as it courses through the module with specified attraction features of the sensor elements refined throughout the molecule's path. The refined information from the interactively programmed individual sensors provides finer and finer determinations of the molecule's size or class potentially down to its exact composition, including isomerization or, in some cases, optical orientation. Volatilization increases as T in the liquid phase is raised. Different VOCs will partition differentially between gas and liquid as T is changed. A controlled heating of the liquid can be employed in analysis for refining the data from the VOC sensing arrays. The differences in VOC presentation as the liquid exposes the gas phase elements in a temperature dependent process become a facet the ML/AI can incorporate in the pattern recognition and signature creation accomplishments. The device is monitoring a multiplicity of compounds in parallel as each molecule progresses through analysis. As molecules become proximal to sensor elements at different times and at different programmed sensor conditions, the analysis progresses in series, dependent on movement and interactions through the sensor layers. Machine-learning/artificial-intelligence (ML-AI) results may be incorporated as a contribution to programming the circuitry.

Signatures can be analyzed independently, as averages, and/or in combination, to suggest disease status, and to thereby recognize a disease signature at any stage starting from the onset of the disease with maximum sensitivity and selectivity. By measuring signal amplitudes of the VOCs, especially of the same VOC under differing attraction conditions, the present device(s) and methods can provide a mathematical strength or probability value and help to gauge the status of a disease which a skilled practitioner may use to assess progress and efficacy of a particular treatment or treatments. Such guidance allows for best practices to be significantly improved.

Detection of volatile components in an environment is an accepted measurement tool. Over several decades, applications, of "artificial noses" with improving sensitivities and repertoires of sensors have been reported. A description of the basic concept can be found, for example, in a 1999 Scientific American article: "How close are artificial noses to development and what are the potential uses?" Authored by Steven Sunshine of Cyrano Sciences, Inc., a company that specializes in industrial quality control and environmental hazards such as purity of components for manufacturing and fuel leaks. Suggested Medical uses included the analysis of biological samples, for example, to detect diabetes. Other specialized applications may involve explosive detection, fruit ripening and spoilage, emissions from automobiles, etc. Many of these devices feature advantageously applied specificity characteristics of attractants such as synthetic polymers and metal oxides to deliver channelized information. A major improvement over the early applications is the use of patterns, or collections of compounds, for example, to distinguish qualities or types of industrial fuels or to detect levels or ratios of compounds to differentiate food ripeness from spoilage. The present invention extends these potential uses by providing devices with improved sensitivity and thus useful over a broad, nearly unlimited range of detection applications assessing both volatile and dissolved molecules.

While VOCs are receiving heightened scrutiny because of their high information content and rapidly improving assaying methods and dedicated devices, many important informative compounds, including bio-active compounds, are too large or have insufficient partial pressures that render volatilization impossible for inclusion in a VOC molecular fingerprint or signature.

VOC detection devices have been described in detail for example in U.S. patent application 63/017,693; Ser. No. 17/244,140 and PCT/US21/36044, the disclosures of which are hereby included in their entireties by reference. Developers are continuously improving the capabilities of electronic noses using tried and true sensors such as metal oxides. See, for example, "Robust and Rapid Detection of Mixed Volatile Organic Compounds in Flow Through Air by a Low Cost Electronic Nose", by Huang and Wu, published Aug. 21, 2020, wherein acetone, ethanol and isopropyl alcohol were detection targets, indicating that cross referencing a plurality of sensors within an analytical algorithm appears to offer detection advantages.

BRIEF DESCRIPTION OF THE PRESENT INVENTION

Miniaturization of sensor elements has continued to drive further applications in fields of environmental safety, medical diagnostics, weather, natural and anthropomorphic contributions to localized and global climate change, as well as many other specialized interests. One such strategy for using micro-devices has been to rely on an interaction between a chemically adsorbent or interactive layer and electrical induction. Specificity of the sensor, i.e., the ability to differentiate a large number of distinct or related molecular types is required for broad-based applicability of sensing devices that are suitable for use across a variety of applications, for example, diagnosing specific diseases and developmental stages in single cell organisms, plants, animals, humans, etc.

Single walled carbon nanotubules (SWNTs) and other carbon substrates such as thin or single layer graphene provide both a large surface to volume ratio to facilitate sensor—molecule interaction, and electrical conductivity that facilitate signal transduction. Zuniga, et al, described such an application using a coating of nucleic acid on a carbon surface to selectively interact with carbon containing (organic) molecules freely moving in a gaseous environment, hence the generic name, volatile organic hydrocarbons (VOCs). Nanotube sensing surfaces may be decorated with nucleic acid, e.g., DNA or RNA prepared with the natural bases or with bases in addition to the genetic coding bases. For example, one or more biopolymer, e.g., an oligonucleotide, such as single stranded DNA, may be prepared in distilled water at a convenient concentration, e.g., about 500 to 1000 µg/ml; about 600 to 900 µg/ml; about 650 to 750 µg/ml, etc. The bare nanosensor is exposed to a drop shape aliquot of decoration solution sufficient to coat the sensing element. A microliter or less is sufficient for most elements. The drop is left for a period of time to allow the decoration to diffuse and optimize alignment with multiple decorations on the element surface. A time of 30 to 60 minutes produces acceptable decorating results. An inert gas, e.g., nitrogen or argon, may be streamed to remove the water as vapor. The decorated elements are thus ready for use in analyzing VOC performance. These concentrations volumes, times, etc., are not intended to be limiting, but may be deemed appropriate for best mode disclosure.

Flushing with inert gas and/or heating can be used to cleanse the sensor arrays between assays. The data processing apparatus preferably includes rezeroing between each sample run. Cleansing can be monitored for completeness by keeping the sensors in operative mode continuously or over timed intervals during the cleanse. Quality control monitoring can signal the operator to intensify cleansing including periodic chemical assisted cleansing.

For example, an oxidizing agent can be added to the flushing gas or a liquid based cleanse can allow reorientation of the functionalizing molecules. Gas and/or liquid may be used to cleanse either or both the VOC sensor elements and the graphene based sensors. A liquid cleanse may allow freer movement of the decoration by providing an aqueous zone for diffusion and repositioning. The cleanse may include new decoration molecules in the solution. Additional molecules in the cleanse solution may provide dilute ions or polar molecules to facilitate movement and repositioning and/or replacement of the decorations. A bleaching agent may improve the cleanse. It may be delivered as a gas or in solution. For example, a halogen gas, a peroxide (e.g., $H_2O_2$), triplet oxygen, perborate (e.g., $NaBO_3$). $SO_2$, $H_2SO_3$, $H_2SO_3^-$, $SO_3^{-2}$, $S_2O_4^{-2}$, $BH_4^-$, borohydride, $OCl^-$, $Cr_2O_7^{-2}$, $MnO_4^-$, $CH_3COOH$, $O_2^{-2}$, etc., may react with the surface molecules to move or remove molecules interfering electronic signaling. Such supercleanse may be performed periodically or as indicated by system self-diagnosis to improve sensor functioning. A cleanse may follow initial decoration and precede a second or subsequent decoration to increase sensor performance perhaps by freeing the decoration molecules to align with others for maximum stability of signal.

In the patent applications incorporated by reference above, nano-sensor elements (NSEs}, each including at least one sensing surface, are capable of, for example, of field-effect transistor (FET) or other physico-electrical property/activity. Such structures include, but are not limited to: semi-conducting nano-wires, carbon nano-tubes—including single-wall carbon nano-tubes, chitosan-cantilever based, synthetic polymers—including dendrimers, plasmon resonance nano-sensors, Förster resonance energy transfer nano-sensors, paramagnetic compounds, surface active crystals, vibrational phonon nano-sensors, magnetically resonant compositions, optical emitting or transforming compositions, optical frequency (or wavelength) based nano-sensors (sensitive to photon transmittance, absorption, reflection, energy modulation, etc.).

Nano FETs and other nano-sensor formats generally operate by changing electrical properties as a substance comes in close proximity to the sensor. The interaction between electrons of the sensed molecule and the sensor surface perturbs the steady state of that surface to elicit its signal. The altered distribution of electrons induced by a proximal molecules, (depending on the design of the nano-sensor) changes one or more electrical properties, e.g., impedance, resistance-conductivity, capacitance, inductance, etc., and thus the physical movement of a detectable particle, e.g., an electron, a photon, etc.

The present invention features improvements based on one or more of these concepts. The invention provides a complex interacting structure allowing improved differentiation, sensitivity and specificity for detection a large variety of VOCs in the gas phase and larger molecules that tend to remain in the liquid fraction. As VOCs and solvent are vaporized from the liquid fraction, the concentrations of the larger, non-volatile or less volatile biomolecules increases. The partitioning of VOCs between phases as concentrations change may be one variable used for characterizing of identifying a VOC. As larger molecules become more concentrated, intermolecular attractions will increase as the ability of solvent to separate them lessens. Complexes formed between receptive molecules will interact with the sensors in manners distinct from the parts that form the complex. These newly formed compositions provide additional relevant responses for signature definition.

Sensors are disposed in a multi-layered stack of sensor arrays in a three-dimensional configuration with the sensor elements controllable in real-time for adjusting the sensing parameters of any activated sensor and its near neighbors. In the liquid environment, each sensor array is porous in two dimensions to the solvent, usually water. In stacked arrays in the liquid phase biomolecules are mobile between layers. Similarly, in the gaseous environments, the vapor molecules are free to move in three dimensions. A barrier impermeable to liquid, but freely permeable to vapors, may be installed to distinguish the liquid and gas sensing zones. Such impermeable barrier is especially useful in low or zero gravity environments and also allows for configurations where the liquid phase is not necessarily below the gaseous phase.

This three-dimensional format featuring controlled movements of sensed molecules can be applied to distinguish a currently sensed molecule from other molecules that may appear similar on that one sensor. The actively sensing element may continue to maintain close or tight proximity to the molecule with signal strength changing as the sensor parameters change and/or neighbor sensors may be engaged to fine tune the identification of that molecule. It is well understood and recognized that certain tuned parameters will decrease rather than increase interaction with the subject molecule and that this decreased interaction will aid in molecular characterization and identification of the subject molecule.

Preferably the stacked sensor elements are distributed across and through sequential layers of a mesh form, e.g., like a woven fabric, sponge-like, or porous formation. Solid strands forming the 3-D mesh pattern may be configured as crossing strands, e.g., at 90° to cross links or may include multiple crossing patterns such as 60° angles. The crossing fibers may contribute to a three-dimensional network. While each direction of mesh fiber may support sensor elements along its length, sensor strands may alternate side by side or be disposed in only a subset of directional strands. Sensors may be sited at fiber intersections and/or between intersections. A class of strands may lack sensors, for example, only providing structure and/or controlling circuitry. A strand may sport identical sensors along its length or may present sensors differentially decorated. Sensors may be individually controlled or in some configurations or sequences, a plurality of sensors may be sited as a pod acting in close proximity or unison. Sensors in pods may be controlled individually or, for example, may share a controlled T. Different decorations on individual sensors can competitively attract vapor molecules. V, V change frequency, or other controlled parameter may be applied as attraction differentiating tools independent of identical or different decorations.

Strands of the fabric may include a core of synthetic polymer (including biopolymer), semi-conducting or metallic like conducting strands, carbon fibers, etc. At a base surface in the stack, the fibers preferably include constant or variable electrical resistance to allow controlled heating (i.e., controlled T) of the entire layer or portion thereof. Convective, electromagnetic or other heating functions may be used at the designers and/or operators discretion. Cross fibers in the weave may be used to control T or in preferred embodiments to control the heating of specific sensor elements. Strands may have different diameters in different layers. Within a layer, stands in one orientation may differ in composition and or thickness from strands in another orientation. A strand may have zones of thinner or thicker diameter or shape. Strands are not necessarily round, but may be any suitable shape, including but not limited to flat, triangular, ellipsoid, etc. Carbon fiber, including single waled nanotubes, are optionally used. Sensors may comprise circuitry without attached sensors. Sensor strands may incorporate embedded circuitry. Layers or strands may communicate wirelessly or though one-, two- or three-dimensional circuitry.

Patterns other than cross-threaded fabric patterns are also possible. For example, a pattern featuring concentric rings, circular or concentric closed patterns of a plurality of linear segments. Rays traversing or connecting inner to outer rings serve as supporting structure and are available for circuitry carrying signals from sensors and/or instructions for modulating sensor characteristics. Such stacked concentric patterns may have a cylindrical shape each layer approximating the diameter of its neighbor(s). A tapered or conical shape may be preferred in some applications.

In especially preferred embodiments impedance is one factor that is controlled as a means of metering or reversing electron flow to control T and sensor base V. NSEs may be any micro or nano sensor element reactive to proximal molecules, whose attraction and proximity is under control of a factor including, but not limited to: base V, fluctuating resonant fields, T, carrier gas, interaction(s) with identical/similar or dissimilar ambient VOCs, photo-activation and/or excitement, sonic stimulation, etc. For example, photo-excitation may serve to dampen or increase sensor attraction to a species of molecular isomer, especially when polarized light is used and the affected molecules are chiral. The fluctuation of tautomeric ratios with different attractions to a sensor element can serve as an important distinguishing feature for identifying the molecule. Electric pulsation and especially high-frequency impedance may serve to control a molecule's movement. One or more portions of the sensing device may monitor impedance change resulting from proximity of a VOC or other gaseous species.

A high density stacking or high-count weave is preferred so that the sensing surfaces interacting zones predominate over non-interacting gas or liquid volume (free space). Limited free space between sensor elements decreases the volume of gas and available distance of a compound from a sensor element and increases availability for proximity interactions. By minimizing dead zones (volumes where molecules are unlikely to interact with a sensor element) readability is improved. The weave however must still permit the flow of the bulk gas or liquid so that compounds of interest have mobility between the available layers. An interlayer distance, when greater than the interweave may permit two-dimensional control between the layers. A fiber to pore ratio between approximately 95:1 and 5:1 is featured in preferred embodiments. Thus ratios of about: 90:1, 85:1, 80:1, 78:1, 75:1, 70:1, 67:1, 60:1: 50:1, 40:1, 33:1, 30:1, 25:1, 20:1, 17:1, 15:1, 12:1, 10:1, 7.5:1, 5:1, and intermediary ratios may be used in select embodiments. In general, but not a requirement, the fiber to pore ratio will be lower in liquid sensing modules since viscosity of the carrier liquid will almost always exceed that of the gaseous environment in the "upper" module. The interlayer distance is often set larger than the pore area to provide improved feasibility for managing flows parallel to the sensor layers.

Embodiments may feature sensors dispersed in a suspension. In this format, the sensor elements would be at the local ambient T that may be zonally controlled, for example using light, container wall or protrusion T, sonic heating, etc. Sensors interacting with a targeted compound would signal, in at least one manner including but not limited to: emitting light, changing absorbance or reflectivity, fluorescing, precipitating, adhering to a container component, changing shape, etc. Such module may be used on conjunction with the liquid and/or gaseous module(s), or to assay a small number of known compounds or classes of compounds.

While each layer is selectively configured with a desired pore-volume ratio, subsequent layers may be similarly configured possibly operating under at least one different controlling factor for proximity binding. For example, cooler temperature in a base layer may be applied as a reservoir or filter to monitor and/or manage timed release of compounds for analysis by subsequent layers. A higher base V, positive or negative, may predominate in introductory layers with subsequent layers expressing reduced V. Time, as an adjunct or alternative to physical location, is another means of managing sensor parameter gradients. For example, a time dimension may be used wherein over a preprogrammed or algorithmically determined (e.g., sensor signal dependent) process, T is raised to provide T dependent partial pressure and kinetic energy increase as potential distinguishing factors useful for compound characterization and differentiation.

In some embodiments, the baser layers can be configured to act at higher Ts, selectively reactive to less volatile components. As the mixture migrates through the stack, T, V or another binding controlling factor, is modulated to increase attraction.

Preferred embodiments feature assaying the identical sample in both liquid and gaseous phase. The sample is introduced into a liquid phase sensing module. The liquid phase module is preferably outfitted with sensor elements exhibiting sensing and reporting capabilities not available in the gaseous environment. Larger, non-volatile or lesser volatile compounds are advantageously detected and quantified in this liquid environment. Proteins, protein fragments, peptides, membrane fragments, virions, bacteria, ions, phospholipids, fatty acids, cytokines, interferons, prostaglandins, vitamins, etc., which might be impossible or difficult to assay using the gas phase sensor are thus assayable simultaneously with VOCs obtained (off-gassed) from the same sample in a single device in a single analytical run. Samples may be pre- or post- processed, e.g., one or more processes including, but filtration, centrifugation chromatography, mass spectrometry, dilution, dialyzing, heating, etc., when desired by the user.

Embodiments may feature different sensor types or classes in the liquid and gaseous module. Each module may include a variety of sensor types. Some examples may feature interacting surfaces including, but not limited to: synthetic polymers, metallic oxides, SWCN, graphene and hybrids thereof, etc., to attractively accomplish and maintain proximity of compounds of analytical interest. Graphene is one example of carbon substrate whose surface can be associated with functional or "decorative" molecules that can be designed or randomly selected for specificity and/or quantitation of compounds of interest. When the decoration may be uncharacterized, e.g., a result from interaction with a mixture of compounds e.g., random nucleic acids, fragments of larger molecules, the algorithms recognize the interactions of each sensor without regard to the decoration. The algorithms have no requirement that any decoration be defined, just how the sensor attracts and interacts with the encountered components. However, any relevant information, including, e.g., decoration binding, may contribute to characterizing or confirming the identity or class of interacting compounds. Rutile crystalline structure semiconducting strands may participate in sensing and/or circuitry.

Graphene sensors may be configured as flat, i.e., essentially planar, save for the bend introduced by the chemical bond angles or may be processed to exhibit a thicker, more three-dimensional structure, for example, a folded, rolled or crumpled graphene. Graphene surfaces may exhibit increased porosity by including gaps or perforations, i.e., discontinuous non-sensor layer portions interspersed within a continuous mesh of structural and/or sensing capable material. Such gaps or perforations may be regularly sized and spaced or may be pseudo-randomly distributed during synthesis. Within a module, layers may incorporate different formats such as synthetic polymer, SWNT, etc. A plurality of liquid and/or gas phase modules may be present or selectively used in some embodiments.

A woven structure featuring sensing elements coated on or around supportive fiber threads 30 allows the supporting matrix to be designed to feature a local information processing function. For example, a sensor indicating near proximity of VOC (or other molecule, e.g., a fatty acid in the liquid module) may initiate a local processing function to alter traits of neighbor sensors. These neighbors may be programmed with altered parameters including, but not limited to: base V, frequency, T, etc., to better characterize or to better attract the molecule at interest. Such processing may be used to track the compound throughout the array providing multi-dimensional binding characteristic information on the electronically monitored compound. Noting the different affinities under different sensing conditions provides valuable information not obtainable in devices without these capabilities. For some applications a module, layer, channel within a module, 2- or 3-dimensional zone may not be activated for the entire assay or a time portion of the assay. The operator will select component portions to address the desired data.

In a simple example, a liquid phase module is disposed at the base of the device. Gravity maintains the liquid in contact with the, e.g., graphene sensor layer(s) and separate from an over-lying gas, aka, "headspace". The headspace may be small, e.g., a minimum separation between the phases, or may be larger with a cross-section that permits sample processing between the liquid and gas phases. However, the headspace may feature active processing components. For example, molecules driven from the liquid phase module may be addressed with electromagnetic radiation, sonic radiation, electric fields and/or magnetic fields to chemically or physically change or fix characteristics. For example, tuning, e.g., a sonic wave system may be employed to resonantly lengthen or unfold a molecule. In select circumstance, the processed molecule may be reintroduced to the liquid phase module having had a different set of atoms now exposed to sensor elements. An electric field may be applied to guide movement of charged particles. When gravity is not the force maintaining lamellar arrangement of the phases, centrifugal action may be applied to drive denser molecules towards the periphery.

In routine operations the liquid phase module may be heated, using bulk and/or targeted energy delivery systems. For example, microwave stimulation may be used to excite aqueous samples to higher kinetic status and thereby drive off volatile compounds as the affinity for water is overcome by their kinetic energy. Sonic influences, vibration, resistance heating, etc., the solvent in the liquid sensing module. Available forces for controlling movements of compounds are known in the art. For example, forces including, but not limited to: electric, magnetic, electromagnetic, acoustic, photo-excitation or photon momentum, etc., may be selected depending on particular circumstance.

Where interest in VOCs predominates and in circumstances where liquid phase analysis is not desired, a gaseous sample may be delivered directly into a gas analysis module or may be delivered through an "empty" liquid module. This allows the NSEs sited in the liquid to interact with vapor molecules. The operator may select this present option whenever, said operator desires such additional analysis.

In environments where a liquid may be unwanted. E.g., where Ts are below the solvent freezing point, the solvent may be corrosive or otherwise damaging, or other operator encountered reason, the device may effect analysis of VOCs "sublimed" out of a solid sample. At the operator's choice, the VOCs may be analyzed using liquid module sensor elements, gas module sensor elements or both.

The present invention may incorporate conventional sample acquisition and preparation processes. For example: urine may be collected from self-voiding into a container, catheterization when necessary or desired, a diaper or other absorbent material, etc.; sweat may be obtained collecting droplets or using absorbents; other liquids may be obtained by available means such as swabbing, spitting, etc. Gaseous samples may be collected as off gasses from a liquid sample or vaporizations off the targeted body area, part or zone.

Preprocessing of samples using components or processes including but not limited to: filters, aerosolizing, centrifugation, chromatography, tagging, mass spectrometry, solvent extraction, dialysis, salting, etc., may be applied in some embodiments. Postprocessing to fragment, separate, and/or refine identification is also anticipated in some embodiments.

As an example, not intended to limit scope of the invention, a urine or blood sample may be filtered or centrifuged to exclude solids which may be separately analyzed. A liquid phase and/or its off-gasses may be fed directly into the device as described above. However, preprocessing as in this example, may be a refining tool. The liquid may be processed through a gas or liquid chromatograph. Dialysis may be used to restrict size of the molecules of interest. GC-MS is a conventional separation and analysis technique that may be enhanced using nanosensor arrays as described herein. Such conventional analyses may be used in series or in parallel with the liquid and or gas phase nanosensor array analysis. For example, GC-MS may be used to confirm findings or to differentiate molecules that may have been detected but not conclusively identified passing through the detector modules.

These multistage analytical procedures can increase specificity, selectivity, quantification and other results obtainable for a sparser repertoire of sensor decorations, such as the nucleic acid functionalities popular in the art.

The invention claimed is:

1. An array of sensor elements (SEs) comprising a plurality of adjustably controlled sensor elements whose sensitivities and/or specificities are differentiated and addressed based on the physical position of each sensor in the array, said plurality comprising a first set and a second set of sensor elements (first set and second set respectively), said first set disposed in a first module having a physical position where said first set contacts molecules of a sample to be sensed earlier than said molecules of the sample to be sensed contact said second set, said first set controlling delivery of molecules of the sample to be sensed by said sensor elements of said second set in a second module physically disposed for subsequent contact with said molecules of the sample to be sensed, said first module and said second module being connected by a vapor permeable passage, said array comprising a plurality of layers having a pattern with crossing strands forming interconnecting intersections.

2. The array of claim 1 wherein said first set-contacts said molecules of the sample suspended or dissolved in a liquid.

3. The array of claim 2 wherein said first set sensors adjustably maintain proximity to a group of molecules with a specificity relatively less specific than said second set.

4. The array of claim 2 wherein said first set sensors are in a zone configured for temperature modulation to release from liquid molecules that on average are lighter than molecules whose solubility is greater.

5. The array of claim 2 wherein said first set sensors maintain greater fractional amounts of molecules, on average, more polar than molecules released to a gas phase.

6. The array of claim 2 wherein said second set sensors contact said molecules of the sample in a gas state.

7. The array of claim 6 wherein said first set liquid off gasses said molecules of the sample into said gas state.

8. The array of claim 7 where said off gassing is controlled by a temperature increase in said liquid.

9. The array of claim 2 comprising a port for delivering a liquid sample.

10. The array of claim 2 wherein said first set contacts said sample suspended or dissolved in a liquid is connected by a vapor permeable passage to sensors disposed for subsequent contact with said molecules of the sample.

11. The array of claim 1 wherein said first set adjustably maintains proximity to a group of said molecules of the sample with a specificity relatively less specific than said second set.

12. The array of claim 1 wherein said first set sensors maintain a preferred proximal association with molecules, on average, heavier than molecules less preferred and more rapid in passing through this part of the array.

13. The array of claim 1 wherein sensor first set said with molecules of a sample are configured to modulate temperature to release from proximal association molecules that on average are lighter than molecules whose proximal association is maintained.

14. The array of claim 1 wherein said first set sensors maintain proximal association with molecules, on average, larger in physical dimension than molecules more rapidly passing through to said second set sensors.

15. The array of claim 1 wherein said first set sensors are configured for temperature modulation to release from proximal association molecules that on average are smaller in physical size than molecules whose proximal association is maintained.

16. The array of claim 1 wherein said first set sensors maintain proximal association with molecules, on average, more polar than molecules more rapid in passing through the array.

17. The array of claim 1 wherein said first set sensors are configured for charge modulation to release from proximal association molecules that on average are less polar than molecules whose proximal association is maintained.

18. The array of claim 1 wherein said plurality of layers is stacked at an angle approximately 90° with respect to the pattern with crossing strands forming interconnecting intersections.

19. The array of claim 1 wherein said intersections comprise communication nodes permitting cross strands to modulate sensing parameters of cross strands.

20. The array of claim 19 wherein said communication nodes participate in a circuit that modulates sensing parameters of set of sensor elements neighbor to a first sensor element.

21. The array of claim 20 wherein said circuit is preprogrammed to modulate said parameters of said set of sensor elements by changing a sensing parameter selected from the group consisting of: voltage, temperature and frequency of alternating charge.

22. The array of claim 20 said circuit is programmed to change a sensing parameter selected from the group consisting of: voltage, temperature and frequency of alternating charge based on a signal from said first sensor element.

23. The array of claim 22 wherein said program incorporates a machine learned component.

24. The array of claim 23 wherein said machine learned component physically tracks a sensed molecule as said sensed molecule transfers from a first sensor element to a second sensor element.

25. The array of claim 19 wherein a semipermeable membrane, permeable to vapor phase, but impermeable to the liquid phase serves as a barrier between said two phases.

26. The array of claim 1 interfaced with a preprocessing sample feeder device.

27. The array of claim 26 wherein said preprocessing sample feeder device comprises a mass spectrometry device.

28. The array of claim 26 wherein said preprocessing sample feeder device comprises a chromatographic device selected from the group consisting of a gas chromatographic device and a liquid chromatographic device.

29. The array of claim 1 wherein said sensor elements further comprise a sensing compound selected from the group consisting of: synthetic polymers, metallic oxides, and hybrids thereof.

30. The array of claim 1 comprising a port for delivering a gas sample.

31. The array of claim 1 comprising a plurality of modules wherein at least two modules are connected by a vapor permeable passage featuring a barrier impermeable to liquid, but freely permeable to vapors.

32. The array of claim 31 wherein at least one of said modules comprises at least one SE comprising graphene.

33. The array of claim 32 wherein said at least one SE comprising graphene is disposed for contacting said sample suspended or dissolved in a liquid.

34. The array of claim 33 wherein said graphene comprises a shape selected from the group consisting of: flat, crumpled, rolled and folded.

35. The array of claim 32 wherein said graphene comprises a shape selected from the group consisting of: flat, crumpled, rolled and folded.

36. The array of claim 32 wherein at least one of said modules comprises at least one SE comprising a single walled carbon nanotube.

37. The array of claim 1 in communication with a data processing computer.

38. An array of sensor elements (SEs) comprising a plurality of adjustably controlled sensor elements whose sensitivities and/or specificities are differentiated and addressed based on the physical position of each sensor in the array, said plurality comprising a first set and a second set of sensors, said first set sensors disposed in a physical position where said first set sensors contact molecules in said sample to be sensed earlier than said molecules of the sample to be sensed contact said second set sensors, said first set sensors controlling delivery of molecules of the sample to be sensed by said second set sensors physically disposed for subsequent contact with said molecules of the sample to be sensed;

wherein said first set sensors are at a temperature less than sensor physically disposed for later contact.

* * * * *